United States Patent
Schneider

(10) Patent No.: US 7,359,055 B2
(45) Date of Patent: Apr. 15, 2008

(54) OPTICAL SENSOR FOR DETERMINING THE CONCENTRATIONS OF DYES AND/OR PARTICLES IN LIQUID OR GASEOUS MEDIA AND METHOD FOR OPERATING THE SAME

(75) Inventor: Reinhold Schneider, Stuttgart (DE)

(73) Assignee: Institut fur Textilchemie der Deutschen Institute fur Textil-und Faserforschung Stuttgart, Denkendorf (DE)

( * ) Notice: Subject to any disclaimer, the term of this patent is extended or adjusted under 35 U.S.C. 154(b) by 197 days.

(21) Appl. No.: 10/538,752

(22) PCT Filed: Sep. 24, 2003

(86) PCT No.: PCT/EP03/10617
§ 371 (c)(1),
(2), (4) Date: Jun. 10, 2005

(87) PCT Pub. No.: WO2004/053467
PCT Pub. Date: Jun. 24, 2004

(65) Prior Publication Data
US 2006/0152730 A1    Jul. 13, 2006

(30) Foreign Application Priority Data
Dec. 11, 2002   (DE) .............................. 102 57 716

(51) Int. Cl.
*G01N 21/00*    (2006.01)

(52) U.S. Cl. ...................... 356/432; 356/436

(58) Field of Classification Search .................. None
See application file for complete search history.

(56) References Cited

U.S. PATENT DOCUMENTS
3,319,514 A    5/1967    McAllister, Jr.
(Continued)

FOREIGN PATENT DOCUMENTS
DE    30 32 150 A1    1/1982
(Continued)

OTHER PUBLICATIONS
Patent Abstracts of Japan, vol. 0133, No. 58, Aug. 10, 1989 & JP 1 119741 A (Nippon Soken Inc.), May 11, 1989.
(Continued)

*Primary Examiner*—Michael P. Stafira
(74) *Attorney, Agent, or Firm*—Venable LLP; Robert Kinberg; Catherine M. Voorhees

(57) ABSTRACT

The invention relates to an optical sensor (1) for determining particle and/or dye concentrations in liquid or gaseous media and to a method for operating the same. The optical sensor (1) comprises at least one measuring head. The measuring head consists of an emitter unit (2) with a semiconductor emitting element (9), which emits visible emission light beams (8), and with a receiver unit (3) with a semiconductor receiving element (10). The portion of the emission light beams (8), which pass through an absorption section containing liquid or gaseous medium, is guided onto the receiving element (10). An evaluating unit (6) is coupled to the measuring head via electric leads (4, 4'), and the received signals, which are present at the output of the semiconductor receiving element (10), are evaluated inside said evaluating unit in order to determine the particle or die concentration.

28 Claims, 1 Drawing Sheet

U.S. PATENT DOCUMENTS

Figure 1:
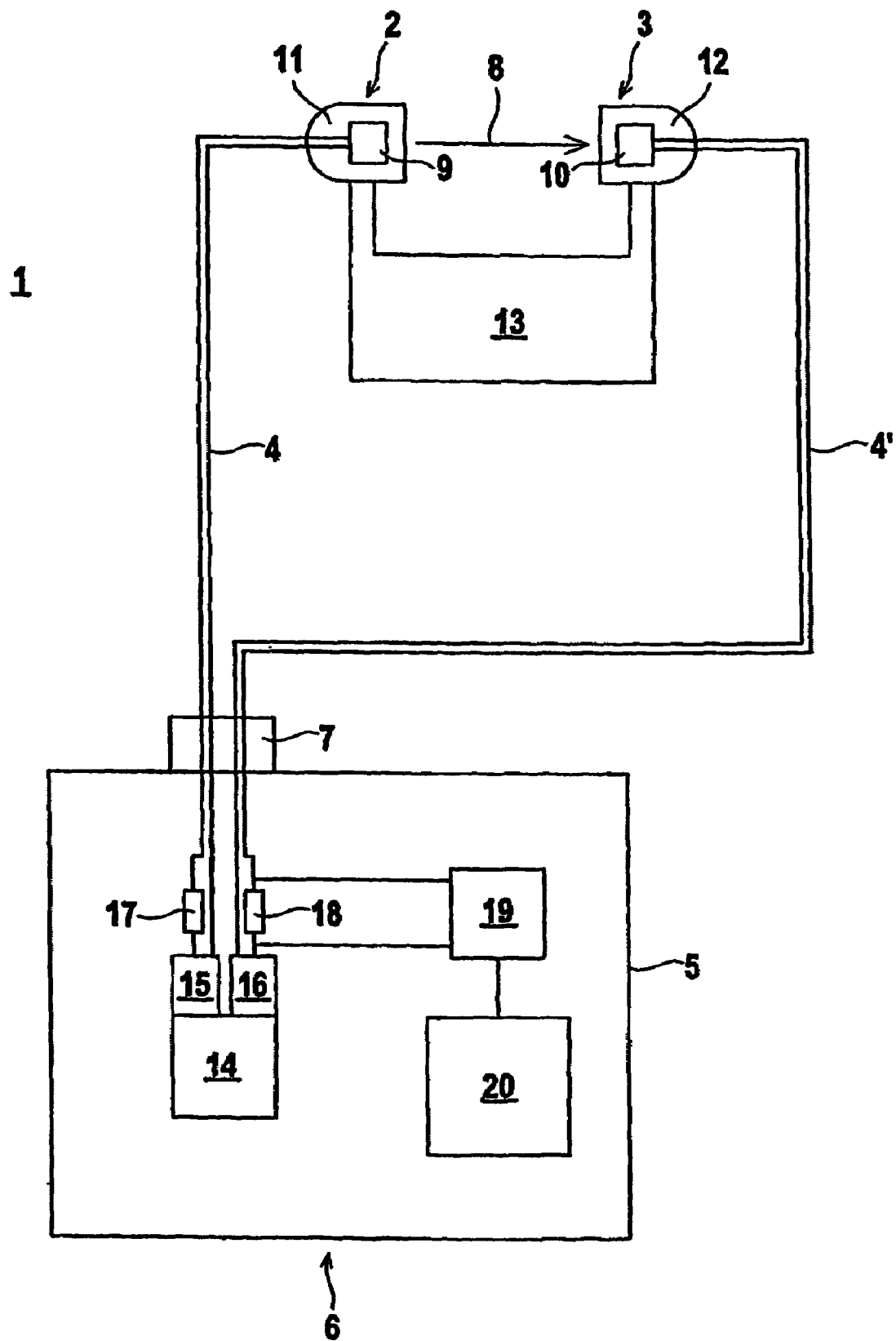

| | | | |
|---|---|---|---|
| 3,850,529 A | 11/1974 | Brugger | |
| 3,890,510 A | 6/1975 | Sturm | |
| 3,892,485 A | 7/1975 | Merritt et al. | |
| 4,699,509 A * | 10/1987 | Kamiya et al. | 356/70 |
| 5,009,064 A | 4/1991 | Grob et al. | |
| 5,230,863 A | 7/1993 | Salpeter | |
| 5,287,168 A | 2/1994 | Poucher et al. | |
| 5,402,242 A | 3/1995 | Nakano | |
| 5,712,710 A | 1/1998 | Karakus et al. | |
| 5,772,589 A | 6/1998 | Bernreuter | |

FOREIGN PATENT DOCUMENTS

| | | |
|---|---|---|
| DE | 42 34 466 A1 | 4/1994 |
| DE | 41 30 931 C2 | 5/1994 |
| DE | 690 28 312 T2 | 1/1997 |
| DE | 196 29 342 C2 | 2/1999 |
| EP | 0 206 433 A2 | 6/1986 |
| WO | WO 99/36772 | 7/1999 |

OTHER PUBLICATIONS

Patent Abstracts of Japan, vol. 0121, No. 00, Apr. 2, 1988 & JP 62 232540 A (Nippon Kokan KK) Oct. 13, 1987.

Senseair: "Theory of Calibration for Sense Air IR Gas Sensors", Technical Note TN-010, Jul 2000, pp. 1-3.

* cited by examiner

US 7,359,055 B2

OPTICAL SENSOR FOR DETERMINING THE CONCENTRATIONS OF DYES AND/OR PARTICLES IN LIQUID OR GASEOUS MEDIA AND METHOD FOR OPERATING THE SAME

CROSS-REFERENCE TO RELATED APPLICATION

This application is a U.S. national-stage application based on PCT International Patent Application No. PCT/EP2003/010617, filed on Sep. 24, 2003, which draws priority from German Patent Application No. 102 57 716.1, filed on Dec. 11, 2002.

BACKGROUND OF THE INVENTION

The invention relates to an optical sensor for determining the concentrations of dyes and/or particles in liquid or gaseous media, as well as to a method for operating the same.

Determining such dye concentrations or particle concentrations in gaseous or liquid media is a problem encountered in different branches of the industry.

In particular, the determination of dye concentrations in liquid media represents a critical element in the waste-water control and furthermore provides an essential parameter for the control and monitoring of rinsing processes, especially when washing dyed and imprinted textiles. With washing operations of this type, the goal basically is to have the shortest possible washing operation and thus also keep the water consumption as low as possible. One approach for optimizing such washing operations consists of controlling the rinsing processes during the washing of textiles in dependence on the actual dye concentrations in the rinsing water. In the process, a rinsing process is stopped if the dye concentration in the rinsing water reaches a specific limit value. As a result, unnecessarily long rinsing processes can be avoided, which causes a reduction in the water consumption and noticeably shortens the duration of the washing operation.

However, this approach requires a continuous control of the dye concentration in the rinsing water during the rinsing processes.

A known method for determining dye concentrations in liquid media is the ECOD measuring technique. With this technique, an electro-chemical determination of the chemical oxygen demand of the liquid medium is realized and the resulting value is used as parameter for the dye concentration.

This technique has the disadvantage that the measuring intervals for determining the chemical oxygen demand are in the order of magnitude of several minutes. Owing to this high reaction time during the determination of measured values, this method is only conditionally suitable for controlling rinsing operations during the washing of textiles.

Optical measuring devices such as spectrophotometers can generally also be used for determining dye concentrations, wherein the disadvantage of these measuring devices lies in the high equipment expenditure. A further disadvantage is that for determining the dye concentration in the rinsing water, samples of the rinsing water must be supplied by means of pumps to flow-through cells in which the dye concentration is then determined. Apart from the required high equipment expenditure, the time required for pumping the rinsing water samples into the flow-through cells is a further disadvantage. As a result, only a time-delayed determination of the dye concentration in the rinsing water is possible, thereby leading to an undesirably high response time for the control of the rinsing operation.

It is the object of the present invention to provide a device and a method which allow a quick and precise determination of the particle and dye concentrations in liquid or gaseous media while the necessary equipment expenditure remains low.

This object is solved with the features disclosed in claims 1 and 23. Advantageous embodiments and useful modifications are described in the dependent claims.

The optical sensor according to the invention, which comprises at least one measuring head, is used for determining particle and/or dye concentrations in liquid or gaseous media. The measuring head consists of a transmitting unit with at least one semiconductor transmitting element that emits visible light rays, as well as a receiving unit with at least one semiconductor receiving element onto which the transmitted light rays that pass through an absorption section filled with liquid or gaseous medium are guided. The measuring head is connected via electrical supply lines to an evaluation unit for evaluating the signals received at the output of the semiconductor receiving element in order to determine the particle and/or dye concentration.

The optical sensor according to the invention has a simple modular design and can thus be produced cost-effectively. The structural dimensions of the measuring head for the optical sensor are small, so that the measuring head can be positioned easily at a measuring location and is flexible for use. The optical sensor is furthermore distinguished by a robust construction which requires almost no maintenance.

One primary advantage of the optical sensor is that its measuring head can also be used in the manner of an immersion sensor module, wherein the optically active sensor elements provided in the measuring head are embodied as semiconductor components. As a result, the measuring head has a small structural size and can be positioned easily in the liquid or gaseous media, such that a defined absorption section that is filled with the liquid or gaseous media to be used is positioned between the semiconductor transmitting element and the semiconductor receiving element.

The transmitting unit with the semiconductor transmitting element and the receiving unit with the semiconductor receiving element are encapsulated, so as to be liquid-impermeable, to prevent damage to the measuring head in particular during the immersion into the liquid medium.

The particle and/or dye concentration in the liquid or gaseous medium is determined by means of an absorption measurement, wherein the length of the absorption section can be specified precisely by securing the transmitting unit and the receiving unit in position on a holder.

With an optical sensor embodied in this way, the particle and/or dye concentration in the liquid or gaseous medium itself can be determined continuously and nearly without delay.

As a result, the sensor signals generated by the optical sensor can be used in particular for a fast and precise control of rinsing processes in a rinsing basin in which dyed textiles are washed.

It is a particular advantage in this case that only the measuring head of the optical sensor is immersed into the liquid medium. The unit for evaluating the sensor signals is positioned outside of the rinsing basin and is connected by means of electrical supply lines to the measuring head.

As a result of its modular design, the optical sensor can be expanded easily by simply connecting several measuring heads to the evaluation unit. As a result, it is possible to determine in particular the dye concentration of liquid media in several basins simultaneously by means of the optical sensor. Accordingly, the rinsing processes in several rinsing basins can be controlled by means of the sensor signals from an optical sensor.

As a result of the modular configuration of the optical sensor, the measuring heads can also be mounted on cells, in particular flow-through cells, thus making it possible to determine the dye concentration or, if applicable, the particle concentration of liquid or gaseous media inside such cells.

According to the invention, the particle and/or dye concentrations in a liquid or gaseous medium are determined on the basis of an absorption measurement, wherein the evaluated sensor signals are the signals received at the semiconductor receiving element, onto which the transmitting rays passing through the absorption section are guided. The determination of the dye concentration in the liquid or gaseous medium is based on the Lambert-Beer Law.

According to the Lambert-Beer Law, the weakening of the transmitting light rays passing through the absorption section filled with the liquid or gaseous medium is defined by an extinction value which is the product of the layer thickness for the absorption section and an extinction coefficient that depends on the wavelength of the transmitting light rays, as well the dyes and/or particles contained in the liquid or gaseous medium.

Accordingly, the absorption measurement realized with an optical sensor is dependent on the sensor parameters, in particular the wavelength of the transmitted light rays.

Prior to realizing the measurements, a calibration operation is therefore carried out to eliminate the dependence of the absorption measurement on sensor-specific parameters, wherein the optical sensor is used to rate the liquid or gaseous medium with predetermined, known particle or dye concentrations. From this, a sensor-specific extinction value is determined as reference value for the values obtained during the subsequent measuring operations.

The measuring results are thus independent of the characteristics of the optical sensor. It is particularly advantageous that optical sensors which do not emit monochromatic light can also be used when eliminating the dependence of the measuring results on the wavelength.

The only requirement for a precise determination of the particle and/or color concentration in the liquid or gaseous medium is that the wavelength range for the transmitting light rays is within the color spectrum of the dye that must respectively be determined.

It has proven advantageous if semiconductor transmitting elements are used which emit visible light rays at the wavelength range of 400-700 nm, wherein the spectral bandwidth for the transmitting light rays preferably is less than 100 nm.

The use of semiconductor transmitting elements which emit light rays at a wavelength range of approximately 470 nm has proven particularly advantageous. With this embodiment of the optical sensor, a broad spectrum of different types of dyes can be detected since these absorb light in the aforementioned wavelength range.

One particularly advantageous use of the optical sensor according to the invention is for determining the soot content and/or the metal abrasion content in engine oils of motor vehicles and the like. Furthermore, the optical sensor according to the invention can be used for determining particle concentrations in exhaust air and thus in the area of emission protection. Finally, the optical sensor can also be used for determining pollutants in waste water.

The optical sensor according to the invention can furthermore be used for determining pollutants in the exhaust gases of motor vehicles.

In addition, the optical sensor according to the invention can be used for the quality control in industrial processes, for example for controlling the pigment or particle concentrations in varnishes as well as the dye concentrations in dye baths used for dying textiles.

The invention is explained in the following with the aid of the drawing which shows in:

FIG. 1 A schematic representation of an exemplary embodiment of the optical sensor for determining dye concentrations in liquid media.

FIG. 1 shows an exemplary embodiment of an optical sensor 1 for determining dye concentrations in liquid media. In general, the optical sensor can also be used for determining particle concentrations. The optical sensor can furthermore be used to determine dye or particle concentrations in gaseous media. The optical sensor 1 is provided with a measuring head, comprising a transmitting unit 2 and a receiving unit 3 which are connected by means of supply lines 4, 4' to an evaluation unit 6 that is integrated into a housing 5.

The measuring head is connected by means of a connector 7 to the evaluation unit 6, wherein several and preferably identical measuring heads can in principle also be connected via separate connectors 7 to the evaluation unit 6.

The transmitting unit 2 is provided with a semiconductor transmitting element 9 which emits transmitting light rays 8. The receiving unit 3 comprises a semiconductor receiving element 10 for receiving the transmitted light rays 8. The semiconductor transmitting element 9 emits visible light rays 8 at a wavelength range of 400-700 nm, wherein the spectral bandwidth for the transmitted light rays 8 is smaller than 100 nm. The semiconductor transmitting element 9 herein can be a light-emitting diode or a laser diode. For the present case, the semiconductor transmitting element 9 is a GaN (gallium-nitride) light-emitting diode with a maximum radiation output at a wavelength of 470 nm.

The semiconductor receiving element 10 consists of a phototransistor, a photodiode, or a photo-resistor. The spectral sensitivity of the semiconductor receiving element 10 is adapted to the wavelength of the transmitting light rays 8. The photosensitive layer of the semiconductor receiving element 10 preferably consists of cadmium selenide, cadmium sulphide or mixtures thereof.

The transmitting unit 2 and the receiving unit 3 for the present case are respectively provided with a light-permeable and liquid-impermeable encapsulation 11, 12 for accommodating the semiconductor transmitting element 9 and/or the semiconductor receiving element 10. The encapsulation 11, 12 consists, for example, of epoxy resins or polymethacrylates. In principle, the encapsulations 11, 12 can also consist of glass, Teflon, or polyolefins.

To form a beam with the transmitting light rays 8, a transmitting optic or a slit-shaped aperture can in principle be provided in the transmitting unit 2. I addition, a monochromatic illuminator can be installed downstream of the semiconductor transmitting element 9 to generate the monochromatic transmitting light rays 8.

An absorption measurement is realized with the optical sensor 1 to determine the dye concentration in a liquid medium. The liquid medium in that case is positioned inside an absorption section through which the transmitting light rays 8 pass. The non-absorbed portion of the transmitting light rays 8 impinges on the semiconductor receiving element 10, thereby generating receiving signals at its output which are then evaluated in the evaluation unit 6.

In principle, the absorption section can be a cell with transparent walls, in particular a flow-through cell. In that case, the transmitting unit 2 and the receiving unit 3 are attached to the outside walls of the cell.

The measuring head for the present embodiment is designed as immersion sensor module which can be immersed into a rinsing basin or the like, so as to directly detect the dye concentration of the liquid medium therein. The optical sensor designed in this way in particular can also be used for determining particle concentrations in engine oils and/or in the exhaust gases of motor vehicles.

For this, the transmitting unit 2 and the receiving unit 3 are secured on a holder 13 in such a way that a measuring gap with predetermined width is created between these two units, thereby defining the absorption section. The positions of the transmitting unit and the receiving unit 3 on the holder 13 are preferably adjustable.

The evaluation unit 6 is used to trigger the semiconductor transmitting element 9 and to evaluate the receiving signals present at the output of the semiconductor receiving element 10. A power pack 14 is provided in the evaluation unit 6 for supplying power to the optical sensor 1. The semiconductor transmitting element 9 and the semiconductor receiving element 10 are respectively supplied with a stabilized constant direct voltage. For this, a voltage stabilizer 15, 16 and a protective resistor 17, 18 are respectively provided for activating the semiconductor transmitting element 9 and/or the semiconductor receiving element 10. To avoid temperature drifting of the receiving signals, a thermistor component such as a NTC resistor can additionally be integrated into the circuit for the semiconductor receiving element 10. A thermistor component of this type can also be used to compensate temperature drifting of the transmitting signals from the semiconductor transmitting element 9. As an alternative or in addition, a suitable software module can also be provided in the evaluation unit 6 for compensating the temperature drifting of the aforementioned components.

The evaluation unit 6 furthermore comprises an analog/digital converter 19 as well as a downstream-connected computer unit 20. The analog receiving signals are digitized in the analog/digital converter 19 and are then read into the computer unit 20 where the dye concentration of the liquid medium is determined by means of the receiving signals which are read in.

The evaluation unit 6 can additionally be provided with an analog or digital display unit, not shown herein, for displaying the actual receiving signals.

The receiving signals, which can be either current signals or voltage signals, are evaluated on the basis of the Lambert-Beer Law.

The optical sensor 1 is calibrated prior to the start of the operating phase for the optical sensor 1. This calibration operation is realized by means of reference measurements during which a liquid medium with a known, predetermined dye concentration for the dye to be determined is respectively arranged in the absorption section.

In the present case, two reference measurements are made during the calibration operation. For the first reference measurement, the absorption section contains a liquid medium without dye. The receiving signals $I_o$ determined during this first reference measurement are stored in the evaluation unit 6. For the second reference measurement, the liquid medium contains a predetermined dye concentration $C_{cal}$ of the dye to be determined, wherein the dye concentration typically is in the range of 0.5-1 g/l. The receiving signals I determined during this second reference measurement are also stored in the evaluation unit 6.

From these two measuring variables, a sensor-specific and dye-specific reference extinction value $E_{cal}$ is then computed in the evaluation unit 6 based on the following equation:

$$E_{cal} = 1 \, g(I_o/I) = \epsilon' d C_{cal}$$

The above equation shows that the reference extinction value $E_{cal}$ is defined by the product of a fictional molar extinction coefficient $\epsilon'$, the layer thickness d for the absorption section, meaning the width of the measuring gap between transmitting unit 2 and receiving unit 3, as well as the predetermined dye concentration $C_{cal}$ of the second reference measurement.

The fictional molar extinction coefficient $\epsilon'$ is defined by the product $$\epsilon' = \epsilon \cdot f,$$

wherein $\epsilon$ is the molar, wavelength-dependent extinction coefficient and f is a correction factor which depends on the structure of the optical sensor 1.

In the operating phase which follows the calibration, the dye concentration of the dye for which the calibration is carried out is determined for the liquid medium to be tested by conducting further absorption measurements with the optical sensor.

The resulting receiving signals $I_{meas}$ which form the actual measuring values are applied to the first reference measurement, in accordance with the following equation:

$$E_{meas} = Ig(I_o/I_{meas}) = KC_x$$

As a result, the extinction value $E_{meas}$ is obtained as actual measuring variable which forms a measure for the dye concentration $C_x$ to be determined.

The proportionality factor K is defined by the following equation:

$$K = \epsilon' \cdot d$$

Following the conversion of the equations for $E_{cal}$ and $E_{meas}$, the dye concentration $C_x$ is determined on the basis of the following relation:

$$C_x = (E_{meas}/E_{cal})C_{cal}$$
$$= [(1gI_0 - 1gI_{meas})/(1gI_0 - 1gI)]C_{cal}$$

This equation shows that the dye concentration $C_x$ to be determined is defined by the measuring values $I_o$, I and $I_{meas}$ as well as the predetermined reference dye concentration $C_{cal}$. The determination of the dye concentration therefore does not depend on the sensor-specific parameters, wherein it is particularly advantageous that no monochromatic transmitting light is required for determining the dye concentration $C_x$.

The following Table shows typical measuring results when using the optical sensor 1 according to the invention for determining various dye concentrations in water as the liquid medium.

TABLE 1

| Dye | concentration in the batch [g/l] | Receiving signal [V] | Dye concentration computed from measuring signal [g/l] | Deviation [g/l] |
|---|---|---|---|---|
| Water | 0 | 2.380 | 0 | 0 |
| Remazol Deep Black N | 0.1 | 1.850 | 0.093 | 0.007 |
| | 0.25 | 1.254 | 0.237 | 0.013 |
| | 0.5 | 0.568 | 0.50 | 0.000 |
| | 1.0 | 0.138*) | 1.00 | 0.000 |
| Remazol Brilliant Blue R | 0.1 | 2.308 | 0.120 | 0.020 |
| | 0.25 | 2.226 | 0.267 | 0.017 |
| | 0.5 | 2.101*) | 0.500 | 0.000 |
| | 1.0 | 1.880 | 0.947 | 0.053 |
| Remazol Brilliant Red F3B | 0.1 | 2.100 | 0.106 | 0.006 |
| | 0.25 | 1.764 | 0.254 | 0.004 |
| | 0.5 | 1.398 | 0.470 | 0.030 |
| | 1.0 | 0.731*) | 1.00 | 0.000 |
| Remazol Yellow GR | 0.1 | 2.000 | 0.120 | 0.020 |
| | 0.25 | 1.600 | 0.307 | 0.057 |
| | 0.5 | 1.213 | 0.520 | 0.020 |
| | 1.0 | 0.657*) | 1.000 | 0.000 |

The above table shows that different dye concentrations were determined for four different dyes. The respectively predetermined dye concentration is entered in the left column of the table. For a comparison, the dye concentrations respectively computed from the receiving signals present in the form of voltage signals are entered. The reference dye concentrations specified for the second reference measurements are respectively marked with *) in the table.

The table furthermore shows that a precise determination of dye concentrations in the liquid medium is given for a broad range of concentrations and a plurality of different dyes. It is particularly advantageous in this case if all measurements can be carried out with the same optical sensor 1 which emits light rays 8 at a wavelength range of 470 nm. Selecting this transmitting wavelength range has proven advantageous since a large number of dyes are highly light-absorbent in this wavelength range.

Depending on the width of the measuring gap in the optical sensor 1, dye concentrations of up to 1 g/l or more can be determined.

The optical sensor 1 furthermore has the considerable advantage of permitting on location and under real-time conditions a determination of the dye concentrations of the respective liquid medium contained in one or several basins by using one or several measuring heads. An optical sensor 1 provided with several measuring heads can simultaneously determine the dye concentration of liquid media at several measuring locations, wherein the measuring signals are evaluated in the evaluation unit 6. The optical sensor 1 thus offers a particularly flexible and cost-effective option for determining the dye concentrations.

If the measuring head is designed as immersion sensor module, it can be used to[1] the dye concentration of the respective liquid media on location, in the basin, and nearly without delay. The optical sensor 1 can therefore be used particularly advantageously for controlling and regulating waste-water control operations. In particular, the optical sensor 1 can be used advantageously for the control of rinsing processes during the washing of dyed and imprinted textiles.

[1]Note: This sentence is incomplete

REFERENCE NUMBER LIST (1) optical sensor
(2) transmitting unit
(3) receiving unit
(4,4') supply lines
(5) housing
(6) evaluation unit
(7) connector
(8) transmitting light rays
(9) semiconductor transmitting element
(10) semiconductor receiving element
(11) encapsulation
(12) encapsulation
(13) holder
(14) power pack
(15) voltage stabilizer
(16) voltage stabilizer
(17) protective resistor
(18) protective resistor
(19) analog/digital converter
(20) computer unit

The invention claimed is:

1. An optical sensor for determining concentration of dyes and/or particles in liquid or gaseous media, comprising:
at least one measuring head with a transmitting unit (2), provided with at least one semiconductor transmitting element (9) which emits visible light rays (8), as well as a receiving unit (3) provided with at least one semiconductor receiving element (10) onto which the portion of transmitted light rays (8) is guided which penetrates an absorption section filled with a liquid or gaseous medium; and
an evaluation unit (6) which is connected via electrical supply lines (4, 4') to the measuring head and is used for evaluating the receiving signals present at the output of the semiconductor receiving element (10) for determining the dye concentration and/or the particle concentration where the transmitting unit (2) and the receiving unit (3) are secured to the at least one measuring head defining the absorption section and can be secured adjustably in different positions on the at least one measuring head.

2. The optical sensor according to claim 1, characterized in that it comprises several measuring heads which are connected to a joint evaluation unit (6).

3. The optical sensor according to claim 1, characterized in that the measuring head, or each measuring head, is embodied as immersion sensor module having a transmitting unit (2) and a receiving unit (3) which are encapsulated so as to be impermeable to liquid.

4. The optical sensor according to claim 3, characterized in that the transmitting unit (2) and the receiving unit (3) are encapsulated with light-permeable materials, at least in the region of the optically active surfaces for the semiconductor transmitting element (9) and the semiconductor receiving element (10).

5. The optical sensor according to claim 4, characterized in that the light-permeable materials are epoxy resins or polymethacrylates, glass, Teflon, or polyolefins.

6. The optical sensor according to claim 3, characterized in that the transmitting unit (2) and the receiving unit (3) are attached to a joint holder (13) for defining the absorption section.

7. The optical sensor according to claim 1, characterized in that a cell filled with a liquid or gaseous medium is provided to form the absorption section, wherein the transmitting unit (2) and the receiving unit (3) are arranged on the external surfaces of this cell.

8. The optical sensor according to claim 7, characterized in that the cell is a flow-through cell.

9. The optical sensor according to claim 1, characterized in that the semiconductor transmitting element (9) is a light-emitting diode or a laser diode.

10. The optical sensor according to claim 9, characterized in that the semiconductor transmitting element (9) emits transmitting light rays (8) in the wavelength range of 400 nm to 700 nm.

11. The optical sensor according to claim 10, characterized in that the spectral bandwidth for the semiconductor transmitting element (9) is less than 100 nm.

12. The optical sensor according to claim 11, characterized in that the semiconductor transmitting element (9) emits light rays (8) at the wavelength range of 470 nm.

13. The optical sensor according to claim 9, characterized in that a monochromatic illuminator, a filter, a gap-type aperture, or a transmitting optic are installed downstream of the semiconductor transmitting element (9), in the beam path for the transmitted light rays (8).

14. The optical sensor according to claim 9, characterized in that the semiconductor transmitting element (9) is supplied with a constant direct voltage.

15. The optical sensor according to claim 1, characterized in that the semiconductor receiving element (10) is a phototransistor, a photodiode, or a photo-resistor.

16. The optical sensor according to claim 15, characterized in that the semiconductor receiving element (10) is supplied with a constant direct voltage.

17. The optical sensor according to claim 16, characterized in that respectively one voltage stabilizer (15, 16) and one protective resistor (17, 18) are provided for stabilizing the direct voltage supplied to the semiconductor transmitting element (9) and the semiconductor receiving element (10).

18. The optical sensor according to claim 16, characterized in that a thermistor component is additionally connected to the semiconductor transmitting element (9) for the temperature compensation of the transmitting signals and/or to the semiconductor receiving element (10) for the temperature compensation of the receiving signals.

19. The optical sensor according to claim 16, characterized in that a software module is provided in the evaluation unit (6) for the temperature compensation of the receiving signals.

20. The optical sensor according to claim 1, characterized in that the evaluation unit (6) is provided with an analog or digital display unit for displaying the receiving signals.

21. The optical sensor according to claim 1, characterized in that the evaluation unit (6) is provided with a computer unit (20) for reading in the receiving signals via an analog/digital converter (19).

22. A method for operating an optical sensor having a semiconductor transmitting element (9) which emits light rays and a semiconductor receiving element (10) onto which the emitted light rays are guided where the emitted light rays penetrate an absorption section filled with liquids or gaseous medium, characterized by the following methods steps:

realizing reference measurements with known dye concentrations or particle concentrations during a calibration operation, using reference media arranged in the absorption section, for determining a sensor-specific and dye-specific and/or particle-specific reference extinction value $E_{cal}$;

subsequently determining extinction values $E_{meas}$ that form actual measuring variables for liquid or gaseous media arranged in the absorption section;

and, following this, determining the dye concentration or particle concentration in the respective liquid or gaseous medium by relating the measured extinction value $E_{meas}$ to the reference extinction value $E_{cal}$, where the reference extinction value is formed according to the equation $E_{cal}=1\ g\ (I_o/I_{cal})$, wherein $I_o$ and $I_{cal}$ represent the signals received at the semiconductor receiving element (10) for a dye-free and/or particle-free reference medium arranged in the absorption section and a reference medium with a predetermined dye concentration and/or particle concentration $C_{cal}$ of the dye and/or particles to be determined.

23. The method according to claim 22, characterized in that the extinction value $E_{meas}$ which forms the actual measuring variable is formed on the basis of the equation $E_{meas}=1\ g\ (I_o/I_{meas})$, wherein $I_{meas}$ is the signal received at the semiconductor receiving element (10) with the liquid or gaseous medium arranged in the absorption section for the dye concentration $C_x$ of the dye and/or the particles to be determined.

24. The method according to claim 23, characterized in that the equation $C_x=(E_{meas}/E_{cal})\ C_{cal}$ is used to determine the dye concentration and/or the particle concentration $C_x$.

25. The use of the optical sensor according to claim 1 for determining the soot content and/or the metal abrasion content in engine oils.

26. The use of the optical sensor according to claim 1 for determining pollutants in exhaust gases of motor vehicles.

27. The use of the optical sensor according to claim 1 for determining the particle concentrations in exhaust air.

28. The use of the optical sensor according to claim 1 for determining pollutants in waste water.

* * * * *